United States Patent [19]
Picha

[11] Patent Number: 5,236,453
[45] Date of Patent: Aug. 17, 1993

[54] MAMMARY IMPLANT AND METHOD FOR REDUCING CAPSULE CONTRACTURE

[76] Inventor: George J. Picha, 6554 Beechwood Dr., Independence, Ohio 44131

[21] Appl. No.: 491,225

[22] Filed: Mar. 9, 1990

[51] Int. Cl.⁵ ............................ A61F 2/12; A61F 2/02
[52] U.S. Cl. ............................................. 623/8; 623/11
[58] Field of Search .................. 623/7, 8, 1, 10, 11, 623/12, 17, 16, 66; 128/DIG. 21

[56] References Cited

U.S. PATENT DOCUMENTS

| | | | |
|---|---|---|---|
| 4,531,244 | 7/1985 | Hamas | 623/8 |
| 4,955,909 | 9/1990 | Ersek et al. | 623/8 |

Primary Examiner—David Isabella
Attorney, Agent, or Firm—Pearne, Gordon, McCoy & Granger

[57] ABSTRACT

A mammary implant is disclosed. Extending from the outer surface of the mammary implant are a plurality of projections of specific combinations of height and width dimensions selected from the group of (1) approximately 750 microns high and approximately 250 microns wide and (2) approximately 1600 microns high and approximately 800 microns wide. Preferred edge to edge spacing distances between adjacent projections and center-to-center spacings between adjacent projections are also disclosed. The projections are thickened near the base.

24 Claims, 2 Drawing Sheets

MAMMARY IMPLANT AND METHOD FOR REDUCING CAPSULE CONTRACTURE

BACKGROUND OF THE INVENTION

The present invention relates in general to mammary implants and in particular to a surface morphology for a mammary implant and a method of increasing nonclassical tissue response in connection with a mammary implant utilizing such surface morphology, which method reduces scar tissue and is believed to reduce the incidence of capsule contracture.

DESCRIPTION OF RELATED ART

When a foreign object is placed in the soft tissue (fascia, muscle, adipose, etc.) of a living body, that body generally attempts to eliminate or isolate the object. Microscopic objects may be engulfed by macrophages and eliminated. Objects which are too large to be engulfed by macrophages tend to be isolated from the body by encapsulation in an envelope of collagen, which is commonly referred to as a fibrous capsule and which is scar tissue. Mammary implants are sufficiently large so as to fall into the latter class and, as foreign objects, are encapsulated by the body in a fibrous capsule, typically in a "classical" tissue response as more fully discussed and illustrated hereinafter.

The fibrous encapsulation of a human mammary implant can commonly lead to a problem referred to as capsule contracture. In capsule contracture, the fibrous capsule, over time, contracts and squeezes the mammary implant. Contracture causes the mammary implant to deform and tighten, losing its natural shape and softness. Classical tissue response is associated with the problem of capsule contracture. Conversely, nonclassical tissue response, as more fully discussed and illustrated hereinafter, reduces the amount of scar tissue and is believed to be associated with less incidence of capsule contracture and/or less severity of capsule contracture. Smooth-surfaced mammary implants generally lead to a classical tissue response, which, as noted above, is associated with capsule contracture.

It was known in the prior art to surround the mammary implant with an external layer of open-cell foam-type sponge material, generally open-cell polyurethane foam. The porosity of the outer layer permitted it to become invaded by body cellular tissue, thereby causing the implant to adhere to the wall of the chest and also to the covering skin and tissues. U.S. Pat. No. 3,336,975 is exemplimatic of this art, and the teachings of that patent are incorporated herein by reference in their entirety.

While polyurethane foam-covered implants permitted tissue ingrowth and thus implant anchoring, the external layer of polyurethane foam was documented to undergo delamination and degradation with subsequent capsule contracture, obviously an undesirable condition.

Some teachings in the prior art have taught the use of a plurality of projections or posts extending from the surface of an implant as a means to reduce the thickness of the fibrous capsule. However, none of these prior art teachings explored the cooperation of the height, width and lateral spacing of projections with respect to the foregoing effect. These prior art teachings include the following, all of which teachings are hereby incorporated herein by reference in their entirety.

U.S. Pat. No. 4,531,244 to Robert S. Hamas teaches a mammary prosthesis comprising an envelope covered by a plurality of posts. According to the Hamas patent, the posts provide and maintain space therebetween such that when the scar tissue of fibrous capsule contracts and compresses the posts, the underlying mammary prosthesis will have a space for displacement and will remain soft. Hamas taught posts having a depth between 1,000 and 10,000 microns (preferably between 1,000 and 5,000 microns) and having a width at the base between 1,000 and 10,000 microns (preferably between 1,000 and 5,000 microns).

However, as will be disclosed hereinafter, the posts taught by Hamas do not teach optimal combinations of height, width, and/or lateral spacing dimensions. This is probably due in part to the fact that the posts taught by Hamas are used principally as mechanical elements to space the scar tissue or fibrous capsule away from the implant surface and not as biological elements to inhibit growth in thickness of the fibrous capsule and/or organization or alignment of the fibrous capsule.

In a Master's Thesis by Shelton Ray Taylor, "The Soft Tissue Response to an Ion Beam Textured Surface", Case Western Reserve University, May, 1980, a study was conducted comparing smooth implants with textured surface implants. The textured surface implants had projections (a) 12 microns high and 4 microns wide; and (b) 31 microns high and 1 micron wide. The author of the thesis concluded that the textured surface implants were encapsulated by a thinner fibrous capsule at 8 weeks, when compared to a smooth surface implant, but that at 18 weeks there was no difference in capsule thickness between the textured and smooth surface implants.

In Picha and Siedlak, "Ion-Beam Microtexturing of Biomaterials", Medical Device and Diagnostic Industry, Vol. 6, No. 4, April 1984, there is described the use of ion-beam milling to produce microprojections on the surface of soft tissue prosthesis such as breast prostheses, and the use of such breast prostheses to reduce capsule contracture. However, no specific optimum size of projections is taught.

In a Master's Thesis by Elizabeth A. Powell, "Changes in the Subcutaneous Tissue Response Caused by Implant Compliance and Surface Morphology", Case Western Reserve University, May, 1982, it was taught that over the six week period following implantation, a textured surface of micropillars 150 microns high, 75 microns wide, with center-to-center spacing between adjacent micropillars of 150 microns, lead to the formation of a thinner fibrous capsule, when compared with a smooth-surfaced implant. However, no optimum range of micropillar sizes for the textured surface were tested, considered, evaluated, or taught.

U.S. Pat. No. 4,608,052 discloses the use of surfaces containing a plurality of posts on implants for use in the human body. However, this reference does not specifically suggest the use of such surface morphologies for mammary prostheses. The reference does suggest the use of posts on surfaces of soft tissue implants, but does not teach any particular height as optimal for the posts and in fact teaches the height of the post as theoretically unlimited (Col. 5, lines 31-35). The '052 patent further teaches that the width of the post is preferably about 50 to 150 microns; and that the edge-to-edge distance between posts is preferably 50 to 150 microns (Col. 5, lines 36-43).

In an Abstract entitled "Effect of Ion-Milled Microstructure on Capsule Formation in Silicones", European Congress on Biomaterials, Sep. 14-17, 1986, Bologna, Italy, page 125, it is taught that the anatomy of the "classical" capsule is altered dramatically by surface projections greater than 100 microns in height, and that when the diameter of a surface projection is greater than 500 microns it begins to interact with the body as a bulk surface and a classical capsule is formed. It further teaches that the number and proximity of blood vessels is greatest for projections that are less than 250 microns in diameter and spacing, but greater than 100 microns in height.

In an Abstract entitled "The Soft Tissue Response to Ion Milled Surface Structures", Transactions of the Society for Biomaterials, 13th Annual Meeting, Jun. 3-7, 1987, New York, N.Y., page 267, textured surface microstructuring is discussed. This Abstract implies that the preferred dimensions of projections on an implant surface are 100 microns wide and 500 microns high.

SUMMARY OF THE INVENTION

In accordance with the present invention, an improved surface morphology for a mammary implant is provided. The surface morphology comprises a supporting structure and a plurality of projections extending from the outer surface, said projections being of specific height and width dimensions which provide improved nonclassical tissue response. In nonclassical tissue response there is a reduced amount of scar tissue, more natural vascularity, blood vessels in closer proximity to the implant surface, and, it is believed, less incidence of capsule contracture and/or less severity of capsule contracture. It has now been discovered that unique combinations of height and width dimensions provide proper tissue penetration with reduction of classical response displayed by continuous or bulk flat surfaces as discussed more fully below.

In accordance with the invention, the projection height and width dimensions are selected from combinations of dimensions comprising (1) an approximate height of 750 microns and an approximate width of 250 microns and (2) an approximate height of 1600 microns and an approximate width of 800 microns. The term "approximate" is defined below. The projection dimensions and spacings are mean values and variations within customary manufacturing methods will occur. A method to reduce the amount of scar tissue and, it is believed, the incidence of capsule contracture around a mammary implant is also disclosed. The method comprises implanting a mammary prosthesis with a surface morphology as described above.

It is most surprising that the improvements of the present invention are exhibited by distinct combinations of projection dimensions as opposed to projections of varying response within a single continuous range of sizes. The reason for the disjunction of the inventive projection dimensions is not fully understood. However, it is believed to be related to the coaction of the projection height and width to provide adequate tissue penetration and sufficient spacing between the projections to accommodate the penetrated tissue without yielding a classical response as by simulation of a bulk or continuous flat surface of significant size.

A fuller understanding of the invention may be had by referring to the following description and claims taken in conjunction with the accompanying drawings.

DESCRIPTION OF THE PREFERRED EMBODIMENT

Figure 1:
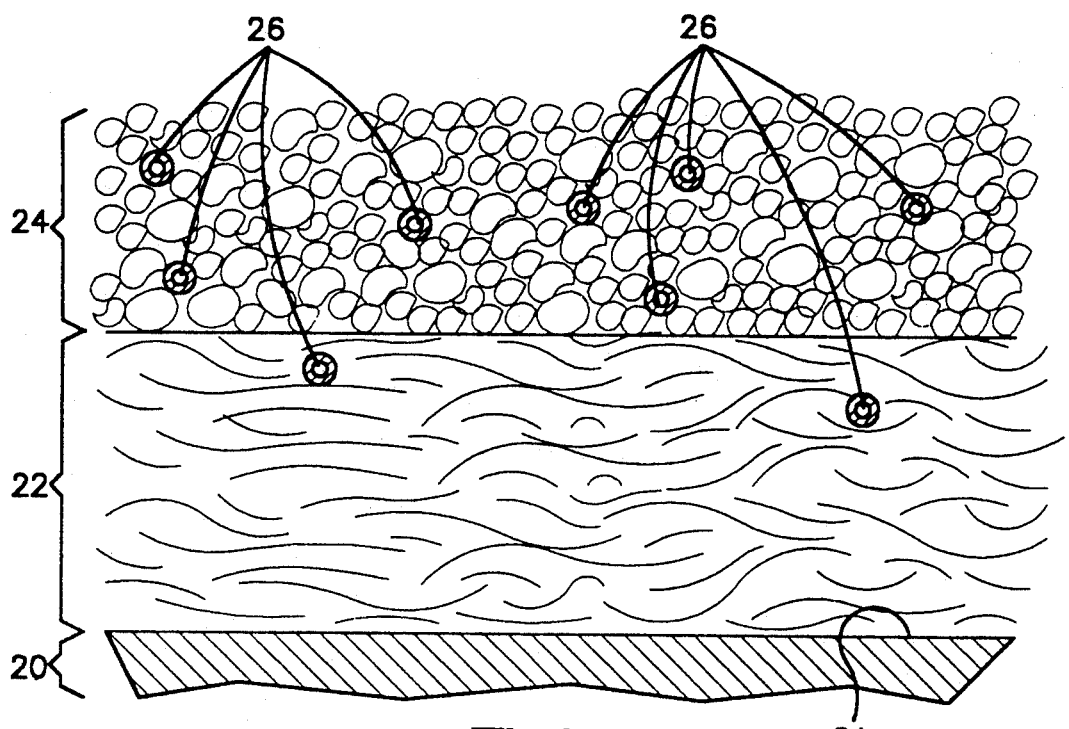
FIG. 1 is a magnified cross-sectional view of a classical fibrous capsule of collagen surrounding a smooth surface mammary implant.

FIG. 1 illustrates what is commonly referred to as the classical tissue response of the body to a smooth surface mammary implant. The surface of the mammary implant is indicated at 21, and the bulk of the mammary implant is partially indicated at 20. A relatively thick, dense fibrous capsule or layer 22 of highly oriented collagen forms around the mammary implant after it is implanted. This layer 22 is scar tissue. Separated from the mammary implant by the collagen layer are a plurality of fat cells 24 or fascia (not shown). Coursing through the fat cells are blood vessels 26. Some blood vessels 26 will also be found in the collagen layer, but these tend not to be in close proximity to the implant surface 21. Further, there is a relatively small amount of vascularization.

Figure 2:
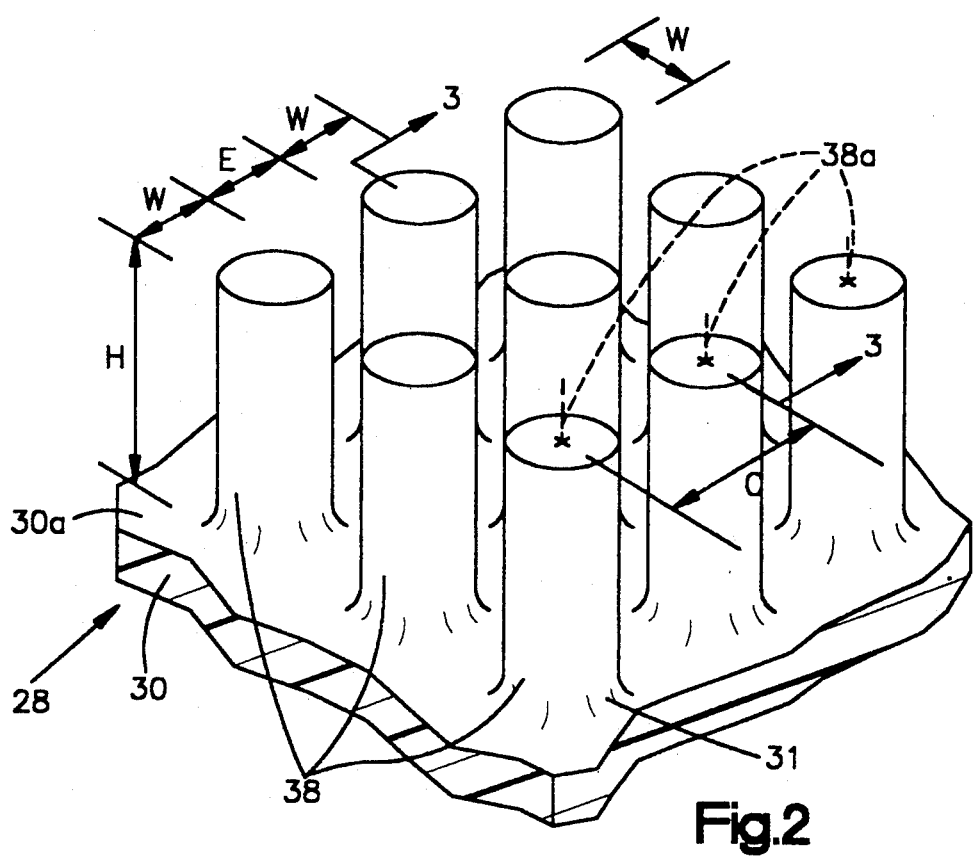
FIG. 2 is a magnified fragmentary perspective view of a mammary implant including a supporting structure having an outer surface provided with a surface morphology in accordance with the present invention, with the support structure of the mammary implant shown in cross-section.

FIG. 2 illustrates a portion of a mammary implant 28 including a supporting structure 30 which typically comprises an envelope for confining suitable silicone gel materials. The supporting structure 30 has an outer surface 30a provided with a surface morphology in accordance with the present invention. The surface morphology is provided at the outer surface 30a of the mammary implant and includes an array of outwardly extending projections 38 of relatively uniform size. The supporting structure 30 and the projections 38 can be made of any suitable inert material as known in the art, including HP Silastic, a high performance silicone elastomer produced by Dow Corning, and other silicone and polymeric elastomers. The projections can be integrally formed with the supporting structure 30. For example, the projections may be formed by molding, by lasers, or by the use of ion-beam milling techniques, which are known in the art and are described in the related art references noted above.

The height (H) and width (W) of the projections 38 may be selected from the combinations of dimensions set forth above. As used in the specification and claims herein, the designation of a numerical value for a parameter such as height or width as "approximate" or "approximately" means a range of values from 10% less than the designated numerical value to 10% more than such value. Thus, an approximate height of 750 microns means a height in the range of from 675 to 825 microns.

The projections 38 are shown as circular in cross section and have a thickened portion or fillet 31 at the base. The thickened portion 31 provides a smooth joint between the projection 38 and the supporting structure 30 which tends to inhibit the development of stress risers. The thickened portion 31 also increases the strength of the attachment between the projection 38 and the supporting structure 30. The concave shape of the thickened portion distributes the stress forces, inhibiting cracking or fracturing.

The projections 38 are generally of a column or shaft-like shape. The projections 38 are preferably circular in cross section, but may also be square, rectangular, triangular, rounded, or any other cross section provided that the ratio of (1) the longest lateral dimension through the centroid of the cross section to (2) the shortest lateral dimension through the centroid of the cross section, is no greater than about 2 to 1. Projections of non-circular cross section should preferably be thickened near the base for the reasons described above.

The top of the projection 38 is shown as flat. It can also be convex or concave. In FIG. 2 the projections are uniformly arrayed. They may be arranged in any suitable manner. The projections may extend along less than all of the outer surface area of the supporting structure.

The projections 38 as shown in FIG. 2 have some sharp edges. Projections with a square or rectangular cross section have more sharp rectangular corners and edges. However, the corners and edges of a projection may be rounded or broken off or otherwise deformed. Some manufacturing techniques may result in these latter-described types of projections. Height is measured from the base of the projection at the supporting structure 30 to the highest point on the projection. Width is measured at the base of the projection without allowing for the thickened portion. If the projection is circular in cross section, the diameter is the width. If the projection is square or about square in cross section, the edge length is the width. Otherwise, the width is deemed to be the average of (1) the longest lateral dimension through the centroid of the cross section and (2) the shortest lateral dimension through the centroid of the cross section.

A lateral spacing (E) corresponds with the edge-to-edge distance between projections. It should be understood that the lateral spacing (E) indicates the clearance or distance between the major adjacent surface portions of neighboring projections. Accordingly, a lateral spacing (E) may be used to characterize, among others, projections having rounded edges or circular cross-sections. If the lateral spacing (E) is too small, the projections will become crowded together and act as a bulk or continuous flat surface. If the lateral spacing (E) is too large, the body again begins to treat the implant as a continuous flat surface.

The preferred width to lateral spacing (W:E) ratio is between 1:0.4 and 1:5. For a 250 micron wide projection, the lateral spacing may range from 100 to 1250 microns. In the case of an 800 micron wide projection, the lateral spacing range is from 320 to 4000 microns. In the case of the 250 micron wide projection, the more preferred W:E ratio is about 1:1. In the case of the 800 micron wide projection, the more preferred W:E ratio is about 1:0.5.

Each of the projection has a central axis or center line 38a. In the illustrated embodiment, the central axis 38a passes through the centroid of the projection 38 and is an axis of symmetry. The center-to-center spacing (C) between adjacent projections is equal to the width (W) plus the lateral spacing (E). Accordingly, the preferred center-to-center spacing (C) for a 250 micron wide projection ranges from 350 to 1,500 microns. The preferred center-to-center spacing (C) for an 800 micron wide projection ranges from 1,120 to 4,800 microns. This corresponds with a preferred width to center-to-center spacing (W:C) ratio between 1:1.4 and 1:6. In the case of the 250 micron wide projection, the more preferred W:C ratio is about 1:2. In the case of the 800 micron wide projection, the more preferred W:C ratio is about 1:1.5.

Figure 3:
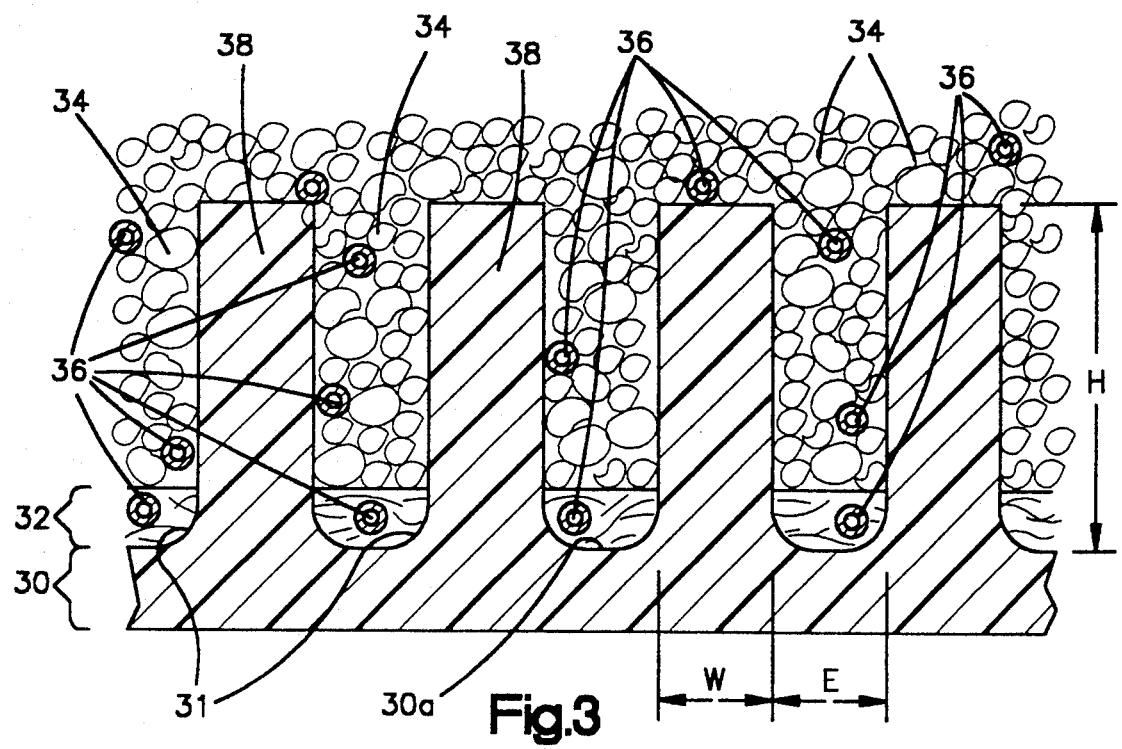
FIG. 3 is a magnified cross-sectional view taken along section line 3—3 of the mammary implant of FIG. 2, as found in vivo.

FIG. 3 illustrates the nonclassical tissue response of the body to the mammary implant 28 of the present invention. A fibrous capsule or layer 32 of collagen is comparatively thin or possibly almost nonexistent. The fibrous capsule is scar tissue. A thin exudate or seroma layer (not shown) may be found between the fibrous capsule 32 and the implant surface 30a. The projections 38 penetrate through the fibrous capsule or collagen layer into the surrounding tissue. The volume between and above projections 38 is substantially filled with fat cells 34 and blood vessels 36. Vascularization tends to be increased. The blood vessels 36 are found very close to the implant surface 30a, including being found in the thin collagen layer 32. The thickened portion of the projection 38 near the base is shown at 31.

The presence of the projections on the surface of the mammary implant has at least three effects. First, the projections provide mechanical anchorage; that is, they penetrate into the surrounding tissue, such as fatty tissue, and hold the implant in place. The tendency for sheer movement, which is a sliding movement along the interface between the implant and the surrounding tissue, is reduced due to a mechanical load transfer from the tissue to the implant. It is more difficult for projections to penetrate fascia or muscle tissue. In contrast, fatty tissue is far more compliant and more easily penetrated by surface projections.

Second, the projections disrupt the long range ordering of the collagen forming the fibrous capsule. The projections form transversely extending obstructions or obstacles disrupting the straight-line or long-range ordering of the collagen, as well as the orientation of blood vessels.

Third, the surface projections can disrupt the polymerization of the collagen forming the fibrous capsule. The interface between the implant and the surrounding tissue is constantly irritated or, through the mechanical sheer of the microstructure with the surrounding tissue, reduces the amount of collagen polymerization.

It is believed that these factors contribute substantially to the nonclassical response of a body to an implant with surface projections, such as the present invention. With regard to mammary implants, the nonclassical response is preferred, since it results in less scar tissue and is believed to result in a reduced incidence of capsule contracture.

The dimensions of the implant projections to lessen the amount of scar tissue and minimize capsule contracture in mammary implants have been determined by the following experimentation. The study utilized implants consisting of disks 1 cm in diameter and 1 mm thick cast from two-part silicone rubber (Dow Corning MDX4-4210). Projections, when present, consisted of a rectangular array of circular cross-section projections with the sharp edges somewhat rounded off. Projections were integrally molded on both sides of the disk.

Fifty male Sprague-Dawley rats, 250–300 gm, were utilized. Four dorsal incisions, bilateral anterior and posterior, were made. The subcutaneous plane was bluntly dissected for some distance away from the incision site and the implants inserted. One face of the disk faced outward toward the dermis; the other faced inward toward the fascia.

A total of 200 disks were implanted. Five surface morphologies and one control were tested, as follows. All dimensions are in microns.

| Projection | Width | Height | Center to Center Spacing | Edge to Edge Distance |
|---|---|---|---|---|
| A | 100 | 500 | 200 | 100 |
| B | 250 | 750 | 500 | 250 |
| C | 400 | 1250 | 650 | 250 |
| D | 400 | 1250 | 800 | 400 |
| E | 800 | 1600 | 1200 | 400 |
| Control | 0 | 0 | N/A | N/A |

An attempt was made to distribute the different surface morphologies, including the flat disk with no surface texture as a control, equally between the four implant sites. After one month, the implants and pelts were harvested and analyzed. Each face of the disk was rated as to whether or not the animal's response to that face was nonclassical, as described above.

The implant surfaces facing the dermis showed very low rates of nonclassical response. This was not unexpected, since little adipose or fat tissue existed in the dermis. The results for the implant surfaces facing the fascia are set forth in FIG. 4.

The fascia on the posterior of the animal contained more fatty tissue than the fascia on the anterior of the animal. The posterior implants were accordingly considered more pertinent.

Figure 4:
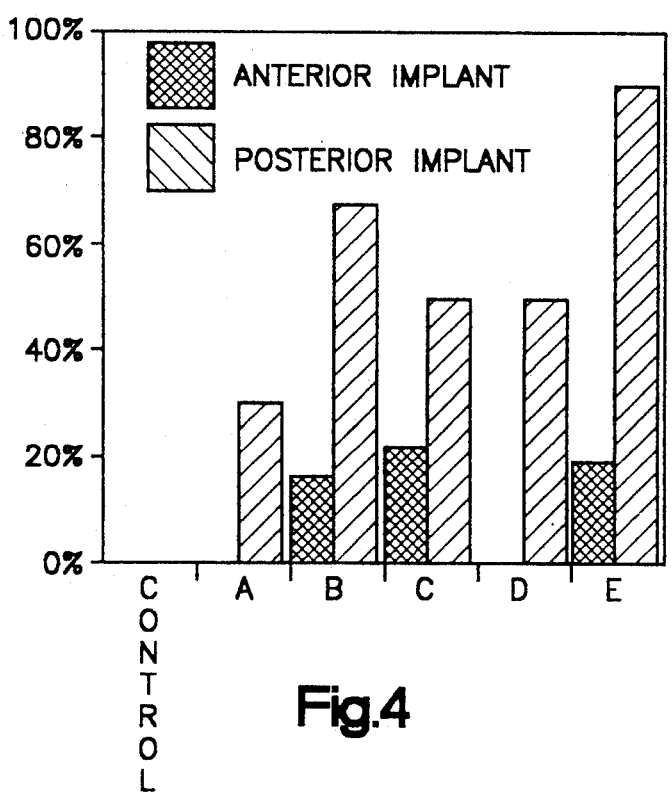
FIG. 4 is a graph illustrating the percentage of implants with selected surface morphologies which elicited a nonclassical response in a study.

It can be seen from FIG. 4 that the B morphology for posterior implants gave a significantly greater percent of nonclassical response than its nearest neighbors in terms of dimensions, those being A, C and D. The percentage nonclassical response achieved by the use of projection B morphology is more than twice that achieved by projection A and about 35% greater than that of projection C. In a similar manner, the percentage nonclassical response achieved by projection E morphology is about 80% greater than that achieved by projection D. These improvements in percentage nonclassical response are most surprising since they arise due to small differences in dimensions and such improvements are associated with disjuncted combinations of height and width dimensions.

Thus, the present inventor has found a synergistic cooperation between specific combinations of height and width projection dimensions for eliciting nonclassical tissue response in mammary implants. The foregoing experiments are considered an appropriate model for human biologic response. These specific projection dimensions are approximately 750 microns high and approximately 250 microns wide and approximately 1600 microns high and approximately 800 microns wide. These combinations of dimensions may be used with a preferred W:E ratio between 1:0.4 and 1:5. In the case of the 250 micron wide projection, the most preferred W:E ratio is about 1:1; in the case of the 800 micron wide projection, the more preferred W:E ratio is about 1:0.5. Mammary implants having a surface morphology in accordance with the present invention are implanted in accordance with known techniques used for implantation of mammary prostheses.

Although the preferred embodiment of this invention has been shown and described, it should be understood that various modifications, replacements, and rearrangements of the parts and methods may be resorted to without departing from the scope of the invention as disclosed and claimed herein.

What is claimed is:

1. An implantable mammary prosthesis having an improved nonclassical tissue response comprising a supporting structure having an outer surface and a plurality of projections extending from the outer surface of said supporting structure, said projections having height and width dimensions selected from the group consisting of (1) approximately 750 microns high and approximately 250 microns wide and (2) approximately 1600 microns high and approximately 800 microns wide.

2. An implantable mammary prosthesis according to claim 1, wherein each of said projections are spaced apart by a lateral spacing sized to allow tissue penetration without promoting classical tissue response.

3. An implantable mammary prosthesis according to claim 1, wherein the projections have a width to center-to-center spacing ratio between 1:1.4 and 1:6.

4. An implantable mammary prosthesis according to claim 1, wherein the projections have a width equal to approximately 250 microns and a width to center-to-center spacing ratio of approximately 1:2.

5. An implantable mammary prosthesis according to claim 1, wherein the projections have a width equal to approximately 800 microns and a width to center-to-center spacing ratio of approximately 1:1.5.

6. An implantable mammary prosthesis according to claim 1, wherein the projections extend from substantially all of the outer surface of said supporting structure.

7. An implantable mammary prosthesis according to claim 1, wherein said projections are arranged in a uniform array, and each of said projections are substantially cylindrical with a thickened area near a base adjacent said outer surface.

8. An implantable mammary prosthesis having improved nonclassical tissue response comprising a supporting structure having an outer surface and a plurality of uniform projections extending from the outer surface of said supporting structure, said projections having a preselected height and width, each of said projections being spaced apart by a lateral spacing sized to allow fascial tissue penetration without promoting classical tissue response, said projections having height and width dimensions selected from the group consisting of (1) a height of from about 675 to about 825 microns and a width of from about 225 to about 275 microns and (2) a height of from about 1,440 to about 1,760 microns and a width of from about 720 to about 880 microns.

9. An implantable mammary prosthesis according to claim 8, wherein said adjacent projections have a width to lateral spacing ratio between 1:0.4 and 1:5.

10. An implantable mammary prosthesis according to claim 9, wherein said projections are arranged in a uniform array, and each of said projections are substantially cylindrical with a thickened area near a base adjacent said outer surface.

11. An implantable mammary prosthesis having improved nonclassical tissue response comprising a supporting structure having an outer surface and a plurality of uniform projections extending from the outer surface of said supporting structure, said projections having a preselected height and width, each of said projections being spaced apart by a lateral spacing sized to allow fatty tissue penetration without promoting classical tissue response, said projections having height and width dimensions selected from the group consisting of (1) a height of from about 675 to about 825 microns and a width of from about 225 to about 275 microns and (2) a height of from about 1,440 to about 1,760 microns and a width of from about 720 to about 880 microns.

12. An implantable mammary prosthesis according to claim 11, wherein said adjacent projections have a width to lateral spacing ratio between 1:0.4 and 1:5.

13. A method to reduce the incidence of capsule contracture around an implantable mammary prosthesis comprising implanting an implantable mammary prosthesis including a supporting structure having an outer surface with a surface morphology, said surface morphology comprising a plurality of projections extending from the outer surface of the supporting structure of said prosthesis, said projections having height and width dimensions selected from the groups consisting of (1) approximately 750 microns high and approximately 250 microns wide and (2) approximately 1,600 microns high and approximately 800 microns wide.

14. A method according to claim 13, wherein each of said projections are spaced apart by a lateral spacing sized to allow tissue penetration without promoting classical tissue response.

15. A method according to claim 13, wherein the projections have a width to center-to-center spacing ratio between 1:1.4 and 1:6.

16. A method according to claim 13, wherein the projections have a width equal to approximately 250 microns and a width to center-to-center spacing ratio of approximately 1:2.

17. A method according to claim 13, wherein the projections have a width equal to approximately 800 microns and a width to center-to-center spacing ratio of approximately 1:1.5.

18. A method according to claim 13, wherein the projections extend from substantially all of the outer surface of said supporting structure.

19. A method according to claim 13, wherein said projections are arranged in a uniform array, and each of said projections are substantially cylindrical with a thickened area near a base adjacent said outer surface.

20. A method to reduce classical tissue response including the incidence of capsule contracture around an implantable mammary prosthesis comprising the step of implanting an implantable mammary prosthesis having a supporting structure having an outer surface and a plurality of uniform projections extending from the outer surface of said supporting structure, said projections having a preselected height and width, each of said projections being adapted to penetrate fascial tissue and said edge to edge distance being spaced apart by a lateral spacing sized to allow fascial tissue penetration without promoting classical tissue response, said projections having height and width dimensions selected from the group consisting of (1) a height of from about 675 to about 825 microns and a width of from about 225 to about 275 microns and (2) a height of from about 1,440 to about 1,760 microns and a width of from about 720 to about 880 microns.

21. A method according to claim 20, wherein said adjacent projections have a width to lateral spacing ratio between 1:0.4 and 1:5.

22. A method according to claim 21, wherein said projections are arranged in a uniform array, and each of said projections are substantially cylindrical with a thickened area near a base adjacent said outer surface.

23. A method to reduce classical tissue response including the incidence of capsule contracture around an implantable mammary prosthesis comprising the step of implanting an implantable mammary prosthesis having a supporting structure having an outer surface and a plurality of uniform projections extending from the outer surface of said supporting structure, said projections having a preselected height and width, each of said projections being spaced apart by a lateral spacing sized to allow fatty tissue penetration without promoting classical tissue response, said projections having height and width dimensions selected from the group consisting of (1) a height of from about 675 to about 825 microns and a width of from about 225 to about 275 microns and (2) a height of from about 1,440 to about 1,760 microns and a width of from about 720 to about 880 microns.

24. A method according to claim 23, wherein said adjacent projections have a width to lateral spacing ratio between 1:0.4 and 1:5.

* * * * *